United States Patent
Desai et al.

(10) Patent No.: US 6,610,856 B2
(45) Date of Patent: Aug. 26, 2003

(54) TINUVIN P-HINDRED AMINE LIGHT STABILIZER AND DERIVATIVES THEREOF

(75) Inventors: Shroj Al Mohitkumar Desai, Pune (IN); Raj Pal Singh, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/201,924

(22) Filed: Jul. 25, 2002

(65) Prior Publication Data

US 2003/0092913 A1 May 15, 2003

Related U.S. Application Data

(62) Division of application No. 09/984,624, filed on Oct. 30, 2001, now Pat. No. 6,492,518.

(51) Int. Cl.⁷ ............................................. C07D 249/18
(52) U.S. Cl. ...................................... 548/110; 548/260
(58) Field of Search .................................. 548/260, 110

(56) References Cited

U.S. PATENT DOCUMENTS

| | | | |
|---|---|---|---|
| 4,709,041 A | | 11/1987 | Mehta |
| 5,021,478 A | * | 6/1991 | Ravichandran et al. |
| 5,362,881 A | | 11/1994 | Leistner et al. |
| 5,480,765 A | * | 1/1996 | Yanagihara et al. ......... 430/338 |
| 6,284,895 B1 | | 9/2001 | Thanki et al. |

FOREIGN PATENT DOCUMENTS

| | | |
|---|---|---|
| DE | 22 58 752 A | 6/1973 |
| DE | 23 52 658 A | 4/1974 |
| DE | 25 00 313 A1 | 7/1975 |
| DE | 26 42 461 A1 | 3/1978 |
| DE | 106 492 C | 12/1989 |

OTHER PUBLICATIONS

Gan H. et al., "A Sterically Controlled Recyclable System: Reversible Photoredox Reactions Between Anthraquinone and Hindered Tertiary Amines", Journal of the American Chemical Society, 1993, Rochester. New York, vol. 115, pp. 8031–8037.

Lutz W.B. et al., "New Derivatives of 2,2,6,6–Tetramethylpiperidine", Journal of Organic Chemistry, Morris Plains, New Jersey, 1962, vol. 27, pp. 1695–1703.

Cygler M. et al., "Conformation of the Piperidine Ring" Journal of Molecular Structure, 1980 Elsevier Scientific Publishing Company, Amsterdam, vol. 68, pp. 161–171.

Orthner L., "Zur Raumchemie des dreiwertigen Stickoffs und von N–Heterocyclen", Justus Liebigs Annalen Der Chemie, 1927, vol. 456, pp. 225–252.

Belostotskii A.M. et al., "Polysubstituted 4–piperidones and 4–piperidols: Synthesis and Spatial Configuration", Bulletin Acad. Sciences USSR Div Chemical Sciences, 1991 Plenum Publishing Corporation, vol. 40, No. 2.2, pp. 421–429.

Patent Abstracts of Japan, JP 11 209 392 A, Aug. 3, 1999, vol. 1999, No. 13.

International Search Report, corresponding to International Application No. PCT/IN01/00190, completed May 15, 2002, 9 pages.

* cited by examiner

*Primary Examiner*—Joseph K. McKane
*Assistant Examiner*—Golam M. M. Shameem
(74) *Attorney, Agent, or Firm*—Burns, Doane, Swecker Mathis, L.L.P.

(57) ABSTRACT

The present invention relates to a photo-stabilizer of the general formula (I):

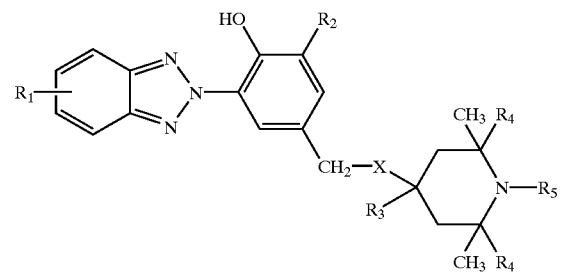

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, $R_3$ is hydrogen, $C_1$–$C_4$ alkyl, $R_4$ is methyl or ethyl, $R_5$ is $C_1$–$C_8$ alkyl, alkyl phenyl, alkoxy, acyl, cycloalkyl and allyl, X is O, NH, $C_1$–$C_8$ alkyloxy and alkylamino (linear or branched), to derivatives and intermediates thereof.

2 Claims, No Drawings

TINUVIN P-HINDRED AMINE LIGHT STABILIZER AND DERIVATIVES THEREOF

This application is a divisional of Ser. No. 09/984,624 filed Oct. 30, 2001 now U.S. Pat. No. 6,492,518.

FIELD OF THE INVENTION

The present invention relates to invention relates to a novel photo-stabilizer of the general formula (I):

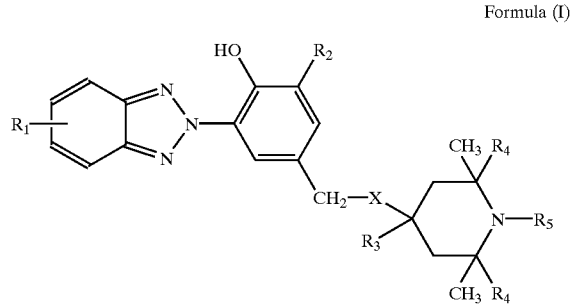

Formula (I)

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, $R_3$ is hydrogen, $C_1$–$C_4$ alkyl, $R_4$ is methyl or ethyl, $R_5$ is $C_1$–$C_8$ alkyl, alkyl phenyl, alkoxy, acyl, cycloalkyl and allyl, X is O, NH, $C_1$–$C_8$ alkyloxy and alkylamino (linear or branched). More particularly, the present invention relates to the said compound of formula I prepared using bromo derivative of Tinuvin P of the general formula (II).

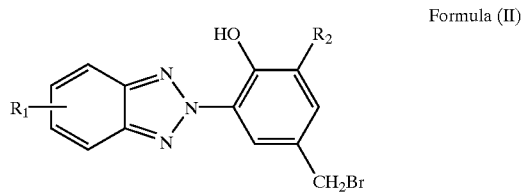

Formula (II)

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, as disclosed in our co-pending patent application Ser. No. 09/749,277 by reacting with a compound of the formula (IV).

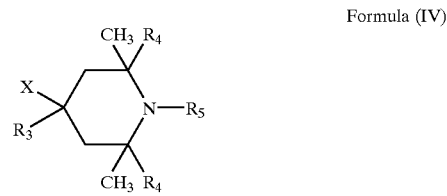

Formula (IV)

wherein $R_3$ is hydrogen, $C_1$–$C_4$ alkyl, $R_4$ is methyl, ethyl, $R_5$ is $C_1$–$C_8$ alkyl, alkyl phenyl, alkoxy, acyl, cycloalkyl and allyl, X is OH, $NH_2$, $C_1$–$C_8$ alkyloxy and alkylamino (linear or branched).

BACKGROUND OF THE INVENTION

Polymers have replaced metals glass, ceramics and papers in packaging, automobiles, building construction, electronics, electrical equipment, furniture, pipes and heavy industrial equipment. In a nutshell, from agriculture to transport and aerospace to food packaging, the use of plastics has become an integral part of our daily life. Polymers, all natural and synthetic, in common use, are susceptible to thermal/photo-oxidative degradation upon exposure to natural and artificial weathering. The deterioration of these polymeric materials is mainly due to the UV portion of sunlight reaching the earth surface. The net result of degradation is the loss in the molecular weight and macroscopic physical properties. In order to avoid this loss, different types of photo-stabilizers have been devised that protect the polymeric substrate from detrimental effect of light. Compatible and mobile light stabilizers usually prove to be best choice to attain the desired photostability. Most of these stabilizers are commercially available and are successfully employed, single and/or in combination with other stabilizers for the polymer stabilization. Researchers have even attempted to study the combined effect screeners, quencher, ultraviolet absorbers and thermal stabilizers. An ample literature on the synthesis and application of these photostabilizers is available to date. Depending upon the type of combination, the effect of the stabilizers can be synergistic and antagonistic. The efficacy of the stabilizer depends on many factors viz. type of combination, proportion of additive, compatibility with the polymer and molecular weight of the stabilizer. Hindered amine light stabilizer (HALS) and benzotriazole based UV absorbers are known to work in synergism and there is no literature on the synthesis of the coupled derivatives of HALS and UV absorbers.

Keeping in view the above-mentioned requirements we have designed and synthesized a novel HALS coupled to an UV absorber. Following patents and literature provide information about synthesis of the photo-stabilizers and the photo-stabilization efficiencies of HALS and UV absorbers solely in presence of each other. JP 200119260: April 2000; U.S. Pat. No. 5,977,219: November 1999; JP 4263874 A2 September 1999; EP 924248 A1: June 1999; U.S. Pat. No. 5,739,348: April 1998; WO 9739052 A1: October 1997; U.S. Pat. No. 5,362,881 November 1994; U.S. Pat. No. 5,086,097 February 1994; Polym. Photochem, 5, 351 (1984), Polym, Degrad, Stab, 8, 133, (1984) and Polym Degrad. Stav. 32, 71 (1991). The process for the synthesis of compound having formula (II) has been disclosed in our co-pending patent application Ser. No. 09/749,277. An online search using SCIFINDER and CHEMICAL ABSTRACT search engines did not provide any positive result for any molecule similar to that synthesised in this invention.

OBJECTS OF THE INVENTION

The main object of the invention is to provide a process for the preparation of novel Tinuvin P-Hindred Amine Light Stabilizer (TP-HALS) derivatives, which can fulfil the above mentioned prerequisites. Moreover, this class of combination of HALS and benzoriazole are known to be compatible with polyolefins, polycarbonate, polystyrene and diene—elastomers and can even be added in an additive proportion to obtain desired photo-stability of various other polymers.

SUMMARY OF THE INVENTION

Accordingly the present invention provides a novel Tinuvin P-Hindred Amine Light Stabilizer derivative of the general formula (I):

Formula (I)

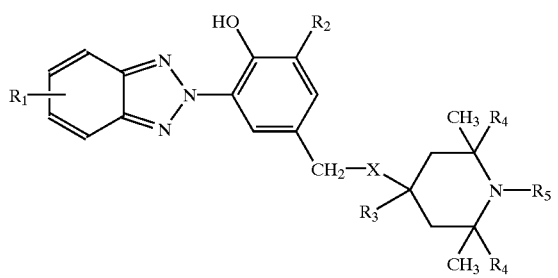

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, $R_3$ is hydrogen, $C_1$–$C_4$ alkyl, $R_4$ is methyl or ethyl, $R_5$ is $C_1$–$C_8$ alkoxy, acyl, cycloalkyl and allyl, X is O, NH, $C_1$–$C_8$ alkyloxy and alkylamino (linear or branched).

The present invention also provides a process for preparation a novel Tinuvin P-Hindred Amine Light Stabilizer derivative of the general formula (I) comprising dissolving a compound having formula (II)

Formula (II)

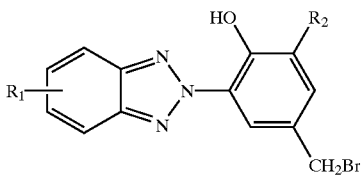

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, with an organic base in a dry organic solvent under inert condition, agitating it initially for a period of 20–30 minutes followed by addition of an hydroxy protecting group and stirring the reaction mixture for 10–14 min under inert atmosphere, followed by evaporating the organic solvent and drying the residue, subsequently dissolving the residue in a low boiling organic solvent followed by filtering the insoluble mass and evaporating the solvent to obtain a compound having general formula (III)

Formula (III)

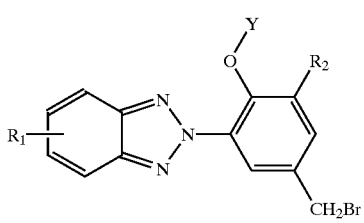

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, and Y is tertbutyldimethylsilyl, tertbutyldiphenylsilyl, dimethyithexylsilyl, benzoyl, benzyl, and acetyl, dissolving compound of formula (III) in a dry organic solvent under inert condition and simultaneously dissolving compound of formula (IV)

Formula (IV)

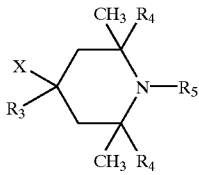

wherein $R_3$ is hydrogen, $C_1$–$C_4$ alkyl, $R_4$ is methyl, ethyl, $R_5$ is $C_1$–$C_8$ alkyl, alkyl phenyl, alkoxy, acyl, cycloalkyl and allyl, X is OH, $NH_2$, $C_1$–$C_8$ alkyloxy and alkylamino (linear or branched) separately but in the same solvent and adding to it a dry metal hydride, agitating the solution for 30–60 minutes, cooling it to 4–8° C. and then adding the solution of compound of formula III gradually over a period of 30–60 minutes, agitating the reaction mixture for 2–4 hrs, followed by refluxing the same for 2–4 hrs, cooling the reaction mixture to room temperature and agitating for 4–6 hrs followed by evaporating the organic solvent under reduced pressure, dissolving the solid mass in water and extracting the product in an organic solvent through repeated extractions and evaporating the organic solvent to obtain a compound of formula (V)

Formula (V)

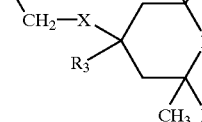

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, $R_3$ is hydrogen, $C_1$–$C_4$ alkyl, $R_4$ is methyl or ethyl, $R_5$ is $C_1$–$C_8$ alkyl, alkyl phenyl, alkoxy, acyl, cycloalkyl and allyl, X is O, NH, $C_1$–$C_8$ alkyloxy and alkylamino (linear or branched), Y is tertbutyldimethylsilyl, tertbutyldiphenylsilyl, dimethylthexylsilyl, benzoyl, benzyl, and acetyl, taking the compound (V) with a hydroxy deprotecting reagent and stirring the reaction mixture at room temperature for 1–3 hrs followed by addition of water and extracting the product in an organic solvent, drying the solvent with an anhydrous inorganic salt after neutralization with an inorganic base an evaporating the solvent to obtain the compound of formula I.

In one embodiment of the invention, the organic solvent used for dissolving the compound of formula (II) is selected from the group consisting of pyridine, dichloromethane, dimethylformamide, tetrahydrofuran, acetonitrile and 1,4-dioxane.

In another embodiment of the invention the base used to react with compound of formula (II) is selected from the group consisting of imidazole, pyridine, 2,6-lutidine, trimethyl amine, mercaptobenzoxazole and alkyl substituted pyridine.

In yet another embodiment of the invention, the hydroxy protecting group is selected from the group consisting of tert-butyldimethylsilyl chloride, tert-butyl-di-phenylsilyl chloride, dimethylthexylsilyl chloride, acetyl chloride, benzoyl chloride, benzyl bromide, benzoic acid, acetic anhydride and acetic acid.

In another embodiment the catalyst used is selected from dimethyl aminopyridine, diethyl aminopyridine, dimethyl aniline, dicyclohexyl carbodimide and hydroxy benzotriazole.

In yet another embodiment of the present invention, the organic solvent used for dissolving the crude mass is selected from the group consisting of dichloromethane, chloroform, acetone, diethyl ether and benzene.

In another embodiment the solvent used to dissolve compound of formula (III) is selected from the group consisting of dimethylformamide, tetrahydrofuran, acetonitrile, 1,4-dioxane and dichloromethane.

In another embodiment the hindered amine having general formula (IV) added to react with compound (III) is selected from the group consisting of 1,2,2,6,6-pentamethyl-4-aminopiperidine, 1,2,2,6,6-pentamethyl-4-piperidinol, 1,2,2,4,6,6-hexamethyl-4-aminopiperidine, 1,2,2,6,6-pentamethyl-4ethylaminopiperidine and its derivatives.

In yet another embodiment the metal hydride is selected from sodium hydride and potassium hydride.

In yet another embodiment the solvent used for extracting the product from the aqueous medium is selected from the group consisting of dichloromethane, dichloroethane, ethyl acetate, diethyl ether, benzene and n-hexane.

In yet another embodiment hydroxy deprotecting agent for deprotecting the compound of formula (V) is selected from the group consisting of tetrabutyl ammonium fluoride, boron triflouride, boron trichloride, boron tribromide, aluminum chloride, sodium bicarbonate, aqueous ammonia, hydrochloric acid, lithium chloride and lithium aluminum hydride.

In yet another embodiment the solvent used for extracting the product from the aqueous medium is selected from the group consisting of dichloromethane, dichloroethane, ethyl acetate, diethyl ether, benzene and n-hexane.

In yet another embodiment the inert gas is selected from Nitrogen and Argon.

In yet another embodiment the inorganic base used to neutralize the solvent fraction containing the product is selected from the group consisting of sodium carbonate, sodium bicarbonate, potassium bicarbonate and potassium carbonate.

DETAILED DESCRIPTION OF THE INVENTION

HALS monomers and some of its derivatives may be prepared by any of the methods that are known in the art including those disclosed in Patents No. JP 53015385 (Jul. 28, 1978), Swiss CH 610898 (May 15, 1979), Swiss CH 605927 (October 1978), Brit. GB 1492494 (November 1977) and Literature: T. Tsuchiya and H. Sashida, Heterocycles, 14, 1925-8 (1980). HALS namely 2,2,6,6-tetramethyl piperidine and 2,2,6,6-tetramethyl-4-piperidinol may be prepared by synthetic route disclosed by W. B. Lutz, S. Lazams and R. I. Meltzer, j Qrg Chem-i 14, 530 (1949) where as the hydroxy benzotriazoles can be prepared by any of the above mentioned methods, disclosed in the patents and literature. All these patents and literature are incorporated herein by reference. The present invention relates to a novel photo-stabilizer; TP-HALS a HALS coupled to an UV absorber and their derivatives. This class of compounds is added to the polymers in order to improve their photo-stability and in turn their life span. They can also be used to obtain photo-stable coatings and paints for out-door applications. HALS and benzotriazoles are found to be compatible with polyolefins, polycarbonate, and a variety of diene elastomers. The novel photo-stabilizer synthesized by the process of the invention bears two different active sites in the same molecule, which are known to work in synergism. The hindered amine site acts as a radical scavenger and the bezotriazole site acts as an UV absorber, thus avoiding the addition of two different additives to the polymer. Moreover, coupling these two different photo-stabilizers not only increase the active sites but also help in increasing the overall molecular weight of the stabilizer, thus decreasing the possibility of its loss due to evaporation, migration/leaching and extraction. These additives have even found applications in a variety of polymers used for food storage, consumer care products and pharmaceuticals, preserving the packaging content from the detrimental effect of high heat and harmful radiation. Moreover, the literature also shows their agricultural applications.

The deterioration of polymeric materials is an inevitable phenomenon and it occurs mainly due to their exposure to the UV portion of sunlight reaching the earth's surface. The net result of degradation is the loss in the molecular weight and macroscopic physical properties. In order to avoid this loss different types of photo-stabilizers have been devised that protect the polymeric substrate from detrimental effect of light. The compatible and mobile light stabilizers usually prove to be the best choice to attain the desired photostability. Most of these stabilizers are commercially available and are successfully employed, single and/or in combination with other stabilizers for the polymer stabilization. Researchers have even attempted to study the combined effect of screeners, quenchers, ultraviolet absorbers and thermal stabilizers.

Ample literature on the synthesis and application of these photostabilizers is available. Depending upon the type of combination, the effect of the stabilizers can be synergistic and/or antagonistic. The efficacy of the stabilizer depends on many factors viz. type of combination, proportion of additive, compatibility with the polymer and molecular weight of the stabilizer. Hindered amine light stabilizer (HALS) and benzotriazole based UV absorbers are known to work in synergism. Moreover, there is hardly any literature on the synthesis of the coupled derivatives of HALS and UV absorbers. The UV absorber of the invention overcomes the prior art disadvantages listed above.

This invention provides a novel photo-stabilizer: Tinuvin P-Hindered Amine Light Stabilizer (TP-HALS) and its derivatives. The derivatives of conventional HALS and benzotriazoles have enhanced photo-stabilization effect, and are useful as additives in a variety of polymers used for food storage, consumer care products (viz. sunscreen/anti-aging lotions) and pharmaceuticals, preserving the packaging content intact.

The process of the present invention is described herein below with reference to the following examples which are illustrative and should not be construed to limit the scope of the present invention in any manner whatsoever.

EXAMPLE 1

Synthesis of 2(2'-tert-butyldimetylsilyloxy-5'-bromomethylpheiiyl)Benzotriazole

This compound was synthesized strictly under dry and inert reaction conditions. In a 100 ML capacity Round Bottom Flask (RB) 2-(2'-hydroxy-5'-bromomethyl phenyl)

benzotriazole (3.0 gms, 0.00986M) was taken along with imidazole (2.1 gm, 0.0295 M) and an inert atmosphere applied using Argon gas. 10 ml of dry pyridine was added and the reaction mixture agitated for 20–60 min The reaction mixture becomes very thick and difficult to stir. To this mixture, tert-butyl dimethyl silyl chloride (5.2 g, 0.0345 M) was added under inert condition and agitation of reaction mixture was continued for 10–14 hrs. After checking the TLC for the completion of the reaction, the pyridine from the RB was evaporated to dryness under vacuum The contents of the RB were consequently dissolved in 15 mL dichloromethane. The insoluble mass was filtered off and the mother liquor was evaporated under vacuum to give (a semi crystalline rust coloured compound) 2-(2'-tert-butyl-dimetylsilyloxy-5'-bromomethylphenyl)benzotzole. The crude product weighed 3.30 gms to give 80% yield. This was purified using column chromatography employing a suitable solvent system. The yield of the pure compound was 76% and its mp.=162–164° C.

EXAMPLE 2

Synthesis of 2-[2'-tert-butyldimetylisilyloxy-5'methyleneoxy ((1",2",2"6",6"-pentamethyl-4"-piperidinyl)phenyl)benzotriazole.

This compound was synthesized strictly under dry and inert reaction conditions. The compound 2-(2'-tert-butyl-dimetylsilyloxy-5'-bromomethylphenyl)benzotriazole (2.1 gms, 0.00501 M) was taken in one 25 mL capacity RB and dissolved in 8 mL dry dimethylformamide (DMF) under Argon atmosphere with stirring. In another two-necked RB, 1,2,2,6,6-pentamethyl-4-piperidinol (1.0356 gm, 0.00601 M) and sodium hydride (0.3 gms, 0.01252 M) were taken and dissolved in 6 mL dry DMF with stirring under Argon atmosphere. This reaction mixture was agitated for almost 60 min and then cooled to 4–8° C. To this reaction mixture the contents of the first RB was added gradually over a period of 30–60 min. This reaction mixture was further agitated for 24 hrs followed by refluxing the same for a period of 24 hrs. The contents of the RB were cooled to room temperature and further agitated for 4–6 hrs at room temperature. The solvent in the RB was evaporated under reduced pressure and the solid mass in the RB was dissolved in 15 mL water and repeatedly extracted with dichloromethane (4×10 mL). Dichloromethane was then evaporated under vacuum at 38° C. over a rotavapor to give pale yellow colored crystalline product 2-[2'-tert-butyldimetylsilyloxy-5'-methyleneoxy((1",2",2",6",6"-pentamethyl-4"-piperidinyl)phenyl)benzotriazole. The TLC showed very little amount of unreacted starting material. The crude yield was 2.22 gms (87%). The product was purified by recrystalization technique using an appropriate organic solvent to get (83%) yield of pure product.

EXAMPLE 3

Synthesis of 2-[2'-hydroxy-5'methyleneoxy ((1",2", 2"6",6"-pentamethyl-4"-piperidinyl)phenyl) benzotriazole The compound 2-[2'-tert-butyldimetylsilyloxy-5'-methyieneoxy((1",2",2",6",6"-pentamethyl-4"-piperidinyl) phenyl)benzotriazole (2.0 g, 0.003937 M) was taken in an RB with a tetrabutyl ammonium fluoride [4.71 mL, 0.004724 M (1.0 M solution in THF)] and the reaction mixture agitated at room temperature for 1–3 hrs under anhydrous conditions, followed by addition of 10 mL water and extraction of the product in DCM (4×10 mL). The solvent was dried with anhydrous magnesium sulfate after neutralization with anhydrous potassium carbonate. Evaporating the solvent gave the product 2-[2'-tert-butyldimetylsilyloxy-5'-methyleneoxy((1",2",2",6",6"-pentamethyl-4"-piperidinyl)phenyl)benzotriazole with a crude yield of 1.39 gms (90%).

Advantages of the Invention

1. The process is economical.
2. The process comprises of commonly available organic reagents and employs mild reaction conditions.
3. High yield ($\geq 75\%$) can be achieved very easily.
4. Reaction can be carried out via very facile route with very simple and moderate reaction conditions.

We claim:

1. A compound having formula (II)

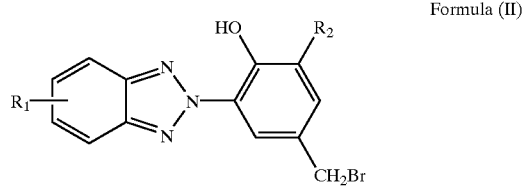

Formula (II)

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl.

2. A compound having general formula (III)

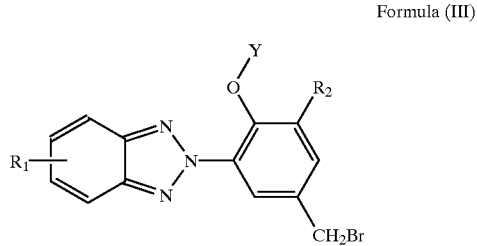

Formula (III)

wherein $R_1$ is hydrogen, halogen, $C_1$ to $C_{12}$ alkyl, alkoxy (linear and branched), $R_2$ is hydrogen, $C_1$–$C_8$ alkyl, cyclopentyl, cyclohexyl or cumyl, and Y is tertbutyldimethylsilyl, tertbutyldiphenylsilyl, dimethylthexylsilyl, benzoyl, benzyl, and acetyl.

* * * * *